(12) United States Patent
Malik et al.

(10) Patent No.: US 8,873,055 B2
(45) Date of Patent: Oct. 28, 2014

(54) OPTICAL TECHNIQUE FOR CHEMICAL AND BIOCHEMICAL ANALYSIS

(71) Applicant: California Institute of Technology, Pasadena, CA (US)

(72) Inventors: Imran R. Malik, Pasadena, CA (US); Xiomara L. Madero, Glendale, CA (US); Erika F. Garcia, Los Angeles, CA (US); Axel Scherer, Barnard, VT (US)

(73) Assignee: California Institute of Technology, Pasadena, CA (US)

( * ) Notice: Subject to any disclaimer, the term of this patent is extended or adjusted under 35 U.S.C. 154(b) by 15 days.

(21) Appl. No.: 13/947,469

(22) Filed: Jul. 22, 2013

(65) Prior Publication Data

US 2014/0036267 A1 Feb. 6, 2014

Related U.S. Application Data

(60) Provisional application No. 61/679,552, filed on Aug. 3, 2012.

(51) Int. Cl.
*G01N 21/25* (2006.01)
*G01N 21/64* (2006.01)

(52) U.S. Cl.
CPC .................................. *G01N 21/64* (2013.01)
USPC ....................................................... 356/417

(58) Field of Classification Search
USPC ................................................ 356/417, 432
See application file for complete search history.

(56) References Cited

U.S. PATENT DOCUMENTS

| 4,930,361 | A | 6/1990 | Nimberger |
| 5,196,830 | A | 3/1993 | Birging et al. |
| 5,272,518 | A | * 12/1993 | Vincent ........................ 356/405 |
| 5,508,197 | A | 4/1996 | Hansen et al. |
| 5,820,265 | A | 10/1998 | Kleinerman |
| 5,871,699 | A | 2/1999 | Ruggeri |
| 6,222,619 | B1 | 4/2001 | Herron et al. |
| 6,441,890 | B2 | 8/2002 | Wardlaw |
| 6,544,734 | B1 | 4/2003 | Briscoe et al. |
| 6,623,696 | B1 | 9/2003 | Kim et al. |
| 6,902,112 | B2 | 6/2005 | Sadler et al. |
| 7,411,792 | B2 | 8/2008 | Richards et al. |
| 7,564,541 | B2 | 7/2009 | Tuschel |
| 7,754,153 | B2 | 7/2010 | Miyamoto et al. |

(Continued)

FOREIGN PATENT DOCUMENTS

| EP | 1972919 | 9/2008 |
| JP | 2002-139418 | 5/2002 |

(Continued)

OTHER PUBLICATIONS

International Search Report mailed on Oct. 16, 2013 for PCT/US2013/051461 filed on Jul. 22, 2013 in the name of California Institute of Technology.

(Continued)

*Primary Examiner* — Abdullahi Nur
(74) *Attorney, Agent, or Firm* — Steinfl & Bruno, LLP

(57) ABSTRACT

Structures and methods are described for optical detection of physical, chemical and/or biological samples. An optical detection structure may include a LED source, multiple filters and single or multiple sample areas. A detector may be used to record a fluorescence signal. The sample area may allow the introduction of removable cartridges.

21 Claims, 4 Drawing Sheets

(56) References Cited

U.S. PATENT DOCUMENTS

| | | |
|---|---|---|
| 8,058,054 B2 | 11/2011 | Owen et al. |
| 8,071,385 B2 | 12/2011 | Haas et al. |
| 8,277,760 B2 | 10/2012 | Lehto |
| 8,395,773 B2 | 3/2013 | Malik et al. |
| 2002/0046614 A1 | 4/2002 | Alley |
| 2002/0160534 A1 | 10/2002 | Herron et al. |
| 2003/0109806 A1 | 6/2003 | Weber et al. |
| 2004/0091862 A1 | 5/2004 | Brandenburg et al. |
| 2004/0152206 A1 | 8/2004 | Davis et al. |
| 2005/0024636 A1 | 2/2005 | Nakamura |
| 2005/0036142 A1 | 2/2005 | Oldham et al. |
| 2005/0042651 A1 | 2/2005 | Vann et al. |
| 2005/0059165 A9 | 3/2005 | Davis et al. |
| 2005/0099621 A1 | 5/2005 | Vaez-Iravani et al. |
| 2005/0109396 A1 | 5/2005 | Zucchelli et al. |
| 2005/0282266 A1 | 12/2005 | Teng et al. |
| 2006/0186346 A1 | 8/2006 | Wei |
| 2006/0211071 A1 | 9/2006 | Andre et al. |
| 2006/0233670 A1 | 10/2006 | Lehto |
| 2006/0289787 A1 | 12/2006 | Ohman et al. |
| 2006/0290934 A1 | 12/2006 | Boekelman |
| 2007/0084279 A1 | 4/2007 | Huang et al. |
| 2007/0272039 A1 | 11/2007 | Hermet et al. |
| 2008/0003649 A1 | 1/2008 | Maltezos et al. |
| 2008/0176230 A1 | 7/2008 | Owen et al. |
| 2008/0176755 A1 | 7/2008 | Amundson et al. |
| 2009/0050209 A1 | 2/2009 | Rautavuori et al. |
| 2009/0176661 A1 | 7/2009 | Harding et al. |
| 2010/0051124 A1 | 3/2010 | Imran |
| 2010/0120164 A1 | 5/2010 | Salafsky |
| 2010/0152066 A1 | 6/2010 | Malik et al. |
| 2010/0184229 A1 | 7/2010 | Haas et al. |
| 2010/0192706 A1 | 8/2010 | Fairs et al. |
| 2010/0321696 A1 | 12/2010 | Malik et al. |
| 2011/0104026 A1 | 5/2011 | Yoon et al. |
| 2011/0151577 A1 | 6/2011 | Zhang et al. |
| 2011/0207137 A1 | 8/2011 | Malik et al. |
| 2011/0306120 A1 | 12/2011 | Nicholls et al. |
| 2012/0003631 A1 | 1/2012 | Yu et al. |
| 2012/0180882 A1 | 7/2012 | Malik et al. |

FOREIGN PATENT DOCUMENTS

| | | |
|---|---|---|
| JP | 2002-214225 | 7/2002 |
| JP | 2012-100549 | 5/2012 |
| WO | 00/21659 | 4/2000 |
| WO | 2007/102713 | 9/2007 |
| WO | 2011-005487 | 1/2011 |

OTHER PUBLICATIONS

Written Opinion mailed on Oct. 16, 2013 for PCT/US2013/051461 filed on Jul. 22, 2013 in the name of California Institute of Technology.

Non-Final Office Action mailed on Oct. 3, 2013 for U.S. Appl. No. 12/638,829, filed on Dec. 15, 2009 in the name of California Institute of Technology.

Final Office Action mailed on Oct. 23, 2012 for U.S. Appl. No. 12/638,829, filed on Dec. 15, 2009 in the name of California Institute of Technology.

Non-Final Office Action mailed on Dec. 16, 2011 for U.S. Appl. No. 12/638,829, filed on Dec. 15, 2009 in the name of California Institute of Technology.

Final Office Action mailed on Oct. 10, 2012 for U.S. Appl. No. 12/820,104, filed on Jun. 21, 2010 in the name of California Institute of Technology.

Non-Final Office Action mailed on Jun. 6, 2012 for U.S. Appl. No. 12/820,104, filed on Jun. 21, 2010 in the name of California Institute of Technology.

International Search Report mailed on Feb. 7, 2011 for PCT/US2010/039389 filed on Jun. 21, 2010 in the name of California Institute of Technology.

Written Opinion mailed on Feb. 7, 2011 for PCT/US2010/039389 filed on Jun. 21, 2010 in the name of California Institute of Technology.

Final Office Action mailed on Sep. 12, 2013 for U.S. Appl. No. 13/009,785, filed on Jan. 19, 2011 in the name of California Institute of Technology.

Non-Final Office Action mailed on May 28, 2013 for U.S. Appl. No. 13/009,785, filed on Jan. 19, 2011 in the name of the California Institute of Technology.

Restriction Requirement issued for U.S. Appl. No. 12/638,829, filed on Dec. 15, 2009 in the name of Imran R. Malik et al.; mailing date: Oct. 20, 2011.

Notice of Allowance issued for U.S. Appl. No. 12/820,104, filed on Jun. 21, 2010 in the name of Imran R. Malik et al.; mailing date: Dec. 24, 2012.

Restriction Requirement mailed on Mar. 5, 2013 for U.S. Appl. No. 13/009,785, filed on Jan. 19, 2011 in the name of California Institute of Technology.

PCT International Search Report mailed on Feb. 3, 2014 for PCT application PCT/US2013/068170 filed on Nov. 1, 2013 in the name of CALIFORNIA INSTITUTE OF TECHNOLOGY.

PCT Written Opinion mailed on Feb. 3, 2014 for PCT application PCT/US2013/068170 filed on Nov. 1, 2013 in the name of CALIFORNIA INSTITUTE OF TECHNOLOGY.

PCT International Search Report mailed on Feb. 17, 2014 for PCT application PCT/US2013/068171 filed on Nov. 1, 2013 in the name of CALIFORNIA INSTITUTE OF TECHNOLOGY.

PCT Written Opinion mailed on Feb. 17, 2014 for PCT application PCT/US2013/068171 filed on Nov. 1, 2013 in the name of CALIFORNIA INSTITUTE OF TECHNOLOGY.

PCT International Search Report mailed on Feb. 6, 2014 for PCT application PCT/US2013/068173 filed on Nov. 1, 2013 in the name of CALIFORNIA INSTITUTE OF TECHNOLOGY.

PCT Written Opinion mailed on Feb. 6, 2014 for PCT application PCT/US2013/068173 filed on Nov. 1, 2013 in the name of CALIFORNIA INSTITUTE OF TECHNOLOGY.

PCT International Search Report mailed on Feb. 17, 2014 for PCT application PCT/US2013/068169 filed on Nov. 1, 2013 in the name of CALIFORNIA INSTITUTE OF TECHNOLOGY.

PCT Written Opinion mailed on Feb. 17, 2014 for PCT application PCT/US2013/068169 filed on Nov. 1, 2013 in the name of CALIFORNIA INSTITUTE OF TECHNOLOGY.

PCT International Search Report mailed on Feb. 14, 2014 for PCT application PCT/US2013/068165 filed on Nov. 1, 2013 in the name of CALIFORNIA INSTITUTE OF TECHNOLOGY.

PCT Written Opinion mailed on Feb. 14, 2014 for PCT application PCT/US2013/068165 filed on Nov. 1, 2013 in the name of CALIFORNIA INSTITUTE OF TECHNOLOGY.

Final Office Action mailed on Jan. 24, 2014 for U.S. Appl. No. 12/638,829 filed on Dec. 15, 2009 in the name of Imran R. Malik et al.

Non-Final Office Action mail on Nov. 26, 2013 for U.S. Appl. No. 13/407,644 filed on Feb. 28, 2012 in the name of Imran R. Malik et al.

Restriction Requirement mailed on Sep. 17, 2013 for U.S. Appl. No. 13/407,644 filed on Feb. 28, 2012 in the name of Imran R. Malik et al.

PCT International Search Report mailed on Feb. 5, 2014 for PCT application PCT/US2013/068172 filed on Nov. 1, 2013 in the name of CALIFORNIA INSTITUTE OF TECHNOLOGY.

PCT Written Opinion mailed on Feb. 5, 2014 for PCT application PCT/US2013/068172 filed on Nov. 1, 2013 in the name of CALIFORNIA INSTITUTE OF TECHNOLOGY.

* cited by examiner

US 8,873,055 B2

OPTICAL TECHNIQUE FOR CHEMICAL AND BIOCHEMICAL ANALYSIS

CROSS REFERENCE TO RELATED APPLICATIONS

The present application claims priority to U.S. Provisional Patent Application No. 61/679,552 filed on Aug. 3, 2012, which is incorporated herein by reference in its entirety. The present application may be related to U.S. Pat. No. 8,395,773, entitled "Optical Devices and Methods for Measuring Samples", filed on Jun. 21, 2010, which is incorporated herein by reference in its entirety.

FIELD

The present disclosure relates to optical detection of chemical, biological and/or physical samples.

SUMMARY

According to a first aspect, a system for optical detection is described, the system comprising: a light source having a first side and a second side; a first optical filter having a first side and a second side, the first side of the first optical filter being substantially close to the second side of the light source; a collimation and/or guidance optics having a first side and a second side, the first side of the collimation and/or guidance optics being substantially close to the second side of the first optical filter; a second optical filter having a first side and a second side, the first side of the second optical filter being substantially close to the second side of the collimation and/or guidance optics; an optics to control stray light having a first side and a second side, the first side of the optics to control stray light being substantially close to the second side of the second optical filter; one or more absorbing layers attached to the second side of the optics to control stray light, wherein the one or more absorbing layers being partially covering the second side of the optics to control stray light, thus allowing the light from the light source to pass through; a chamber containing a sample to be illuminated, the chamber being contained in a cartridge comprising a reflector attached to a first side of the cartridge and a reflective layer attached to bottom of the cartridge, wherein the light emitted by the sample are reflected back to the sample by the reflective layer and guided by the reflector towards a second side of the cartridge; and a detector having a first side and a second side, the first side of the detector being substantially close to the second side of the cartridge, wherein the detector detects the light emitted by the sample.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1:
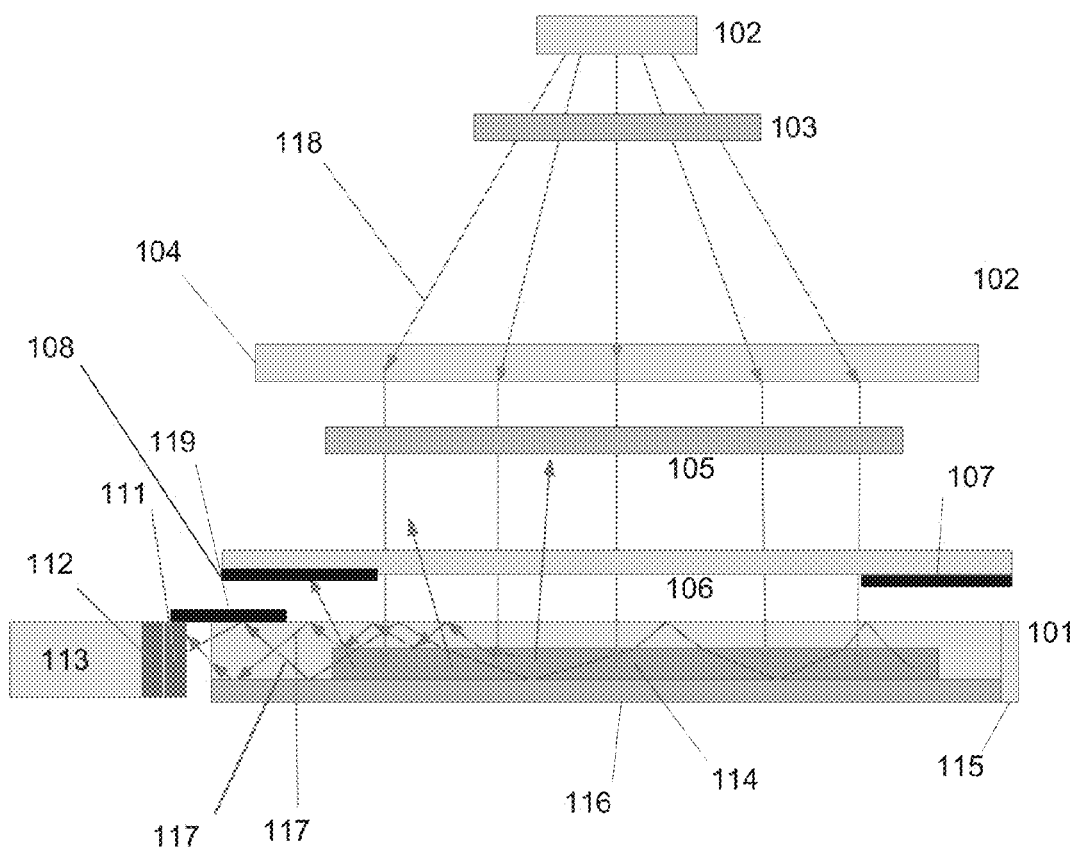
FIG. 1 shows a cross sectional view of an exemplary arrangement of an optical detection structure with top illumination technique.

Throughout the present disclosure, embodiments and variations are described for the purpose of illustrating uses and implementations of the inventive concept. The illustrative description should be understood as presenting examples of the inventive concept, rather than as limiting the scope of the concept as disclosed herein. Like reference numerals indicate corresponding parts in various figures.

Different embodiments of the present disclosure can demonstrate different optical techniques which can allow various types of optical measurements (e.g. absorbance, fluorescence etc.) from numerous sample types. Furthermore, such technique can be coupled with quantitative laboratory methods for chemical and biochemical analysis. For example, the optical technique can be used to obtain fluorescence measurements for real-time polymerase chain reaction (qPCR) and enzyme-linked immunosorbent assay (ELISA). Such technique can have many advantages, for example, (but not limited to the following):
1. Small size.
2. Low cost.
3. Possible lens-less configurations.
4. Can make optics possible without mechanical contact and low alignment requirements.
5. Bubble formation can have little to no effect on the optics.
6. Can allow one the ability to query large surface areas and flat samples.
7. Does not require precise alignments.
8. Does not require tight tolerances.
9. Can make multiplexing possible.
10. High illumination can be possible.
11. Small solid angles, which can be very sensitive.
12. Can be integrated in portable and point of care (POC) instruments.
13. Can work with microfluidic, disposable and many other cartridge types.
14. Can work with many different sample sizes.
15. Can allow the use of low cost LED optical elements.
16. No beam splitter is required, as in confocal designs.
17. Can have the ability to do fluorescence detection without the use of any filters.

According to an exemplary embodiment of the present disclosure, FIG. 1 shows an exemplary arrangement of a top illumination technique, which can be used to detect a sample in a cartridge (101). The exemplary embodiment of FIG. 1 comprises a LED (light emitting diode) source (102), a first filter (103), a collimation and/or guidance optics or a light guide (104), a second filter (105), an optics to control stray light (106), two absorbers (107) and (108) mounted on the two ends of the optics to control stray light (106), a hollow cartridge (101), a detector (113) and a reflector or optics (119). In the exemplary embodiment of FIG. 1, the cartridge (101) comprises a vertical reflector (115) attached to a first side of the cartridge (101), a chamber (114) enclosed inside the cartridge (101) and a reflective back layer (116) attached to the bottom of the cartridge (101). The detector (113) can be placed at a desired distance from a second side of the cartridge (101) and an optics (112) attached to a first side of the detector (113), can further be attached to a third filter (111). The optics (112) and the third filter (111) attached to the first side of the detector (113) can be placed between the second side of the cartridge (101) and the first side of the detector (113). In the exemplary embodiment of FIG. 1, the reflector or optics (119)

can be placed on the top of the second side of the cartridge (101) and the filter (111) to guide the light from the second side cartridge (101) to the detector (113).

In the exemplary arrangement of the top illumination technique as shown in the exemplary embodiment of FIG. 1, the LED (102) can be used to illuminate a sample placed in the chamber (114) from top, where the chamber (114) is enclosed inside the cartridge (101). In some embodiments, other light sources, for example, a LCD (liquid-crystal display) can be used as well. The light guide (104) (either filled or reflective) can be placed at a distance from the LED (102) to capture rays limited to a particular angle. The light guide (104) can be composed of various shapes to match the shape of the chamber (114) being queried in a particular measurement or application. This can allow homogenized beam in addition to having a designed shape of the beam which can match the chamber (114) shape. In lieu of a light guide (104), a lens can also be used. Low cost LED optic lenses and reflectors can be available in a wide range of shapes and sizes which can allow beams and spots of various sizes. Additionally, in some embodiments, mounted high brightness (HB) LED's can be employed as well. In some other embodiments, multiple LED's can be connected together as well to form an array or for multiplexing.

As shown in the exemplary embodiment of FIG. 1, in order to restrict excitation wavelengths below the cutoff, the first filter (103) can be placed between the LED (102) source and the light guide (104). The first filter (103) can either be absorbance or interference type. The first filter (103) can be composed of various materials including, but not limited to plastic, resin, glass etc. To reduce the cost of the optical set-up, very low cost plastic filters (e.g. the filters used in entertainment and architectural industry) can be used as well. In some embodiments, the filter (103) can be put on the LED (102) itself as well. In some other embodiments, dye LED's can be used and can be integrated into optics like waveguides, which can help with the reduction of stray light. In the exemplary embodiment of FIG. 1, the optics to control stray light (106) with two absorbers (107) and (108) mounted on its two ends can be placed in between the cartridge (101) and the light guide (104) to control stray light.

In the exemplary embodiment of FIG. 1, when a sample inside the chamber (114) is illuminated by excitation rays (118) from the LED (102), emission light (117) can be emitted from the sample. Some of this emission light waves (117) can escape from the top. However, a significant portion of the light can be trapped inside the cartridge (101), due to total internal reflection (TIR), and will emit from the side of the cartridge. A material with a higher index of refraction (for example, plastic or some other polymer) can be used to build the cartridge (101), as it will trap more light inside the cartridge (101) due to the critical angle. As a result, taking measurements from the side can be performed. In the exemplary embodiment of FIG. 1, the detector (113) can be placed at a desired distance from a second side of the cartridge (101) and the optics (112) attached to the first side of the detector (113) can be further attached to the third filter (111). The optics (112) and the third filter (111) attached to the first side of the detector (113) can be placed between the second side of the cartridge (101) and the first side of the detector (113). In some embodiments, multiple detectors can be placed at the sides of the cartridge to allow for multiplex detection. Furthermore, each detector can have its own filter. Various kinds of optics can be placed in front of these detectors as well.

In some embodiments, the cartridge (101) can have features built-in that can aid in light collection. The sides of the cartridge (101) can have various optical shapes which can be integrated into the cartridge. In some embodiments, the sides of the cartridge (101) can be a convex shape to guide light from side of the cartridge to the detector (113). In some embodiments, external optical elements can be used as well. In the exemplary embodiment of FIG. 1, the vertical reflector (115) or a light guide element can be used to guide light to various detectors. The back layer (116) of the cartridge (101) can be designed to be reflective in order to direct the light down into sample. Additionally, the reflective back (116) can reflect the light which comes out from the side of the cartridge at angles in the downward direction. The back layer (116) can be made reflective by using metal or by coating the polymer cartridge with metal, such as aluminum. The support on which the cartridge rests (not shown in the figures) can also be made of reflective material (e.g. polished aluminum). In the exemplary embodiment of FIG. 1, the cartridge (101) can go through thermal cycling and can perform qPCR. The cartridge (101) can be used for ELISA or other quantitative techniques as well.

In some embodiments, absorbers can be strategically placed to reduce stray light by absorbing the reflected excitation light. In the exemplary embodiment of FIG. 1, the optics to control stray light (106) with two absorbers (107) and (108) mounted on its two ends can be placed in between the cartridge (101) and the light guide (104) to control stray light. In the exemplary embodiment of FIG. 1, the chamber (114) inside the cartridge (101) can be thin but wide. In the exemplary embodiment of FIG. 1, the sample inside the chamber (114) can be illuminated in such a way as to have sufficient signal for detection of the sample's optical response. Thin designs, such as the chamber (114) can have better thermal response than thick designs. In some embodiments, for thin and wide chambers, which have better thermal characteristics (allowing good thermal dispersion), a wide beam can be used.

Figure 2:
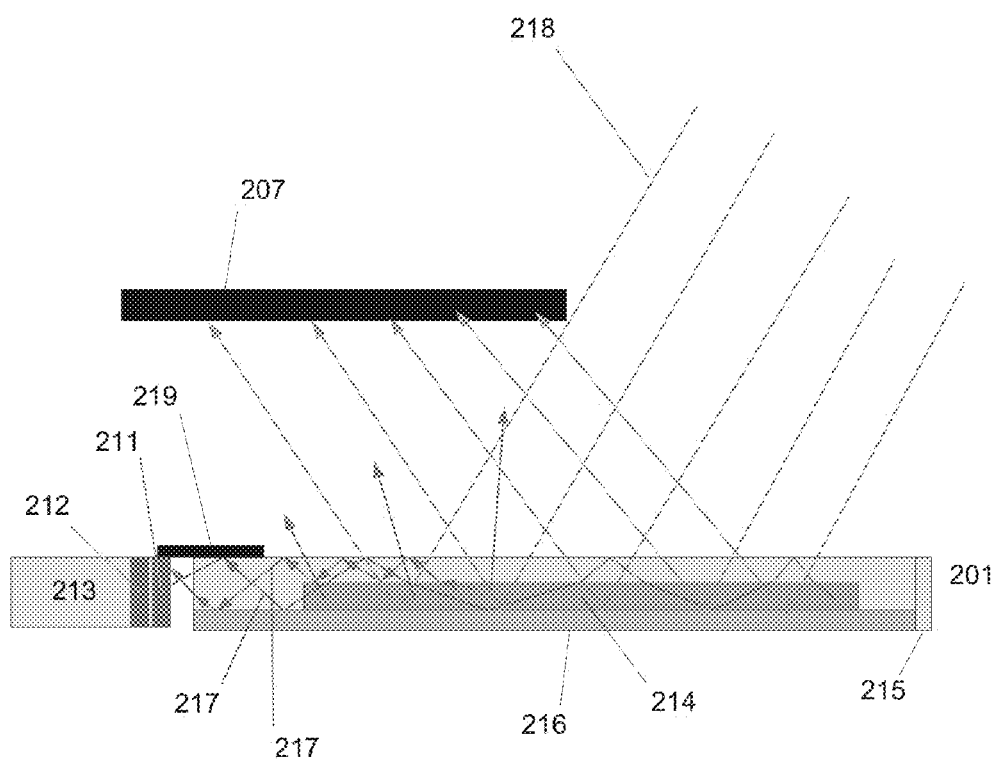
FIG. 2 shows an exemplary arrangement of an angled illumination technique with side detection.

According to an exemplary embodiment of the present disclosure, FIG. 2 shows an exemplary arrangement of an angled illumination technique with side detection. This angled illumination technique, as shown in the exemplary embodiment of FIG. 2 is not limited to sample illumination directly from the top. Similar to the exemplary embodiment of FIG. 1, the exemplary arrangement of FIG. 2 comprises a light source (not shown in the FIG. 2), a hollow cartridge (201), a detector (213) and a reflector or optics (219). Similar to the exemplary embodiment of FIG. 1, in the exemplary embodiment of FIG. 2, the cartridge (201) can comprise a vertical reflector (215) attached to a first side of the cartridge (201), a chamber (214) enclosed inside the cartridge (201) and a reflective back layer (216) attached to the bottom of the cartridge (201).

In the exemplary arrangement of FIG. 2, the detector (213) can be placed at a desired distance from a second side of the cartridge (201) and an optics (212) attached to a first side of the detector (213) can further be attached to a third filter (211). The optics (212) and the third filter (211) attached to the first side of the detector (213) can be placed between the second side of the cartridge (201) and the first side of the detector (213). In the exemplary embodiment of FIG. 2, the reflector or optics (219) can be placed on the top of the second side of the cartridge (201) and the filter (211) to guide the light from the second side cartridge (201) to the detector (213).

In the exemplary embodiment of FIG. 2, the light source to illuminate a sample inside the chamber (214) can be placed at an angle with respect to the cartridge (201). In the exemplary embodiment of FIG. 2, due to the angularly placed light source, the excitation light rays from the light source can be directed at an angle to the cartridge (201) or the sample inside the chamber (214). Since the index of refraction of plastics is more than that of air, if the cartridge (201) is made of plastic, light rays will bend and get into the cartridge (201). Light blocking/absorbing elements (for example, absorber (207)) can be strategically placed so that the reflected light occurring due to top illumination is absorbed and does not bounce around and cause stray light effects.

Figure 3:
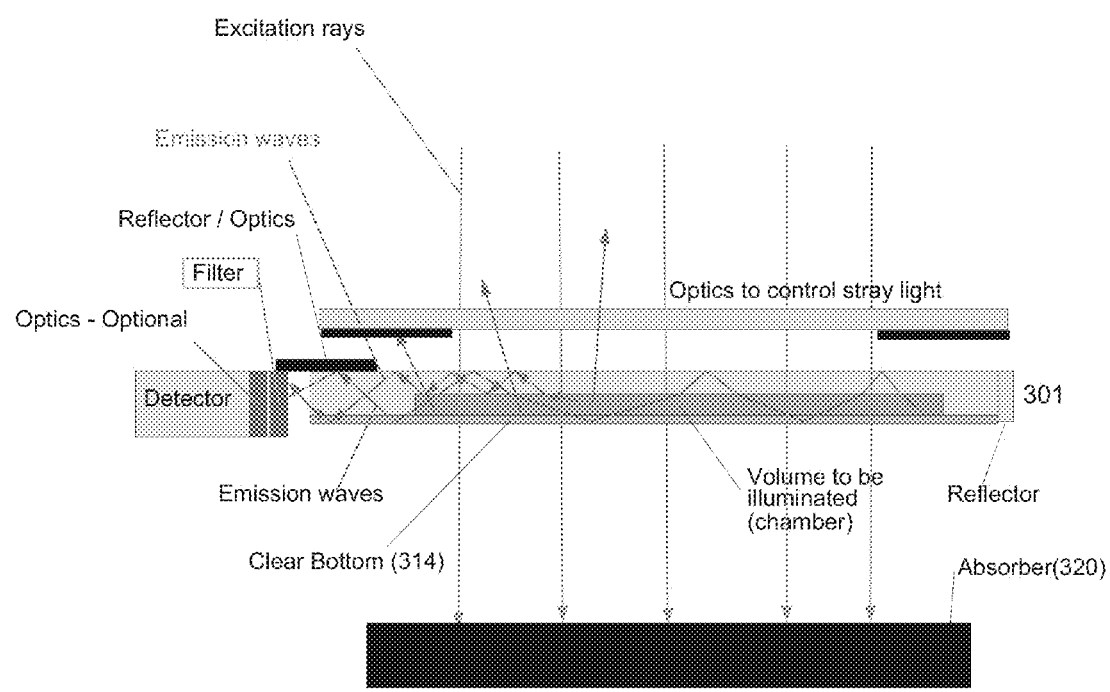
FIG. 3 shows an exemplary arrangement of pass-through irradiation.

According to an exemplary embodiment of the present disclosure, FIG. 3 shows another exemplary arrangement of the top illumination technique with pass-through irradiation. In the exemplary arrangement of FIG. 3, the bottom of the chamber (314) can be made from a clear polymer while an absorber (320) can be placed below the bottom of the cartridge (301). Thus, the excitation will be absorbed. A cavity type structure can also be made to absorb the light. The polymer (which the cartridge (301) is made of) can guide the emission light to the sides by TIR (total internal reflection).

Figure 4:
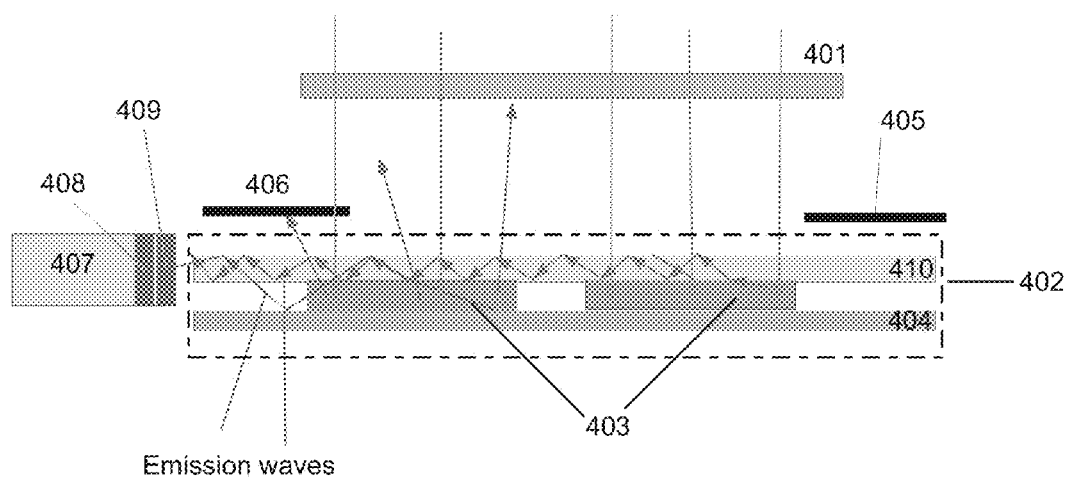
FIG. 4 shows an exemplary arrangement with multiple wells sample area.

In accordance with the present disclosure, the exemplary embodiment of FIG. 4 shows an exemplary arrangement of the top illumination technique with multiple wells, using a common cover film (410). Similar to the exemplary arrangement of FIG. 1, the arrangement of FIG. 4 can comprise a source for illuminating a sample (not shown in the figure), a filter (401) placed between the source for illuminating the sample and a cartridge (402) to trap the emission waves from the samples to be illuminated placed inside multiple chambers (403). The multiple chambers (403) can be sandwiched between the cover film (410) and a reflective back wall (404). Multiple absorbers (for example, absorbers (405) and (406)) can be placed between the cartridge (402) and the filter (401) to eliminate stray light.

In the exemplary embodiment of FIG. 4, the detector (407) can be placed at a desired distance from a second side of the cartridge (402). An optics (408) attached to a first side of the detector (407) can further be attached to a filter (409). The optics (408) and the filter (409) attached to the first side of the detector (407) can be placed between the second side of the cartridge (402) and the first side of the detector (407).

This technique can be amenable to having a compact diagnostic/analysis accessory which can be attached to a cell phone. In such cases, the LED on a cell phone can be used for illumination and the cell phone camera can act as a detector. The filter (401) can be incorporated to select the wavelength required. Such as a cell phone, or another example of accessory device, may have its own excitation source. Light guides can be used to direct the emission into the camera after passing through the filter.

In some embodiments, depending on the user needs, emission and/or excitation filters can be integrated into the design. For example, if the emission and excitation wavelength are a great deal apart, such that the excitation wavelength does not overlap with emission wavelength of interest, then the excitation filter can be omitted. In such cases, a UV LED can be used to excite visible emitting dyes. On the other hand, if the excitation is well guided and does not reach the detector in appreciable quantity (e.g. the excitation does not undergo significant total internal reflection (TIR) or is predictable, such as, at high temperatures where fluorescence of DNA (deoxyribonucleic acid) dyes goes very low), then both filters can be omitted. The use of a laser diode can achieve this as well.

The above mentioned technique, as shown in the exemplary embodiment of FIG. 4, can be arranged in such a way as to comprise an array of sample areas (wells), where each well can be queried to make a robust qPCR/isothermal fluorescence reader or fluorescence reader instrument with easy to no filter requirements, of low cost and small size. Various excitation sources can be used in turn or simultaneously as well. Air can be used to heat and cool or maintain the temperature for isothermal etc. In some embodiments, if the bottom is reflective, a contact cooling technique can be used (for example, Peltier cooling). Furthermore, there exist many low cost laser diodes, laser, LEDs and other types of light sources available for numerous dyes. In many cases, it may not be desired that a high degree of collimation be achieved. In such cases, this can be done using absorbing structures which don't let excess excitation light go to the detectors (being guided by TIR, stray or taking other paths).

In the exemplary optical techniques of the present disclosure, CD laser diodes and optics, and rotating disc platforms can be used as well. In some embodiments, vertical cavity surface emitting lasers (VCSELs) can also be used for excitation. In cases where a cover film is used (like in hybridization, PCB or metal cavity—the walls can be opaque) the emission light can travel in the cover film since in most cases it will have a higher index of refraction, as shown in FIG. 4. The excitation light at some angles will be trapped in the cover film by TIR. The cover film can either lay flat or tilted. In cases of opaque side walls the fraction of light going to the sides can be less than that with a transparent cartridge.

In some embodiments, there is light trapped in the cover film which can be used for detection. In such cases, a prism structure can be used to collect emission. For example, each well of a 96-well plate (as known in the art) can receive excitation illumination, one at a time. The cover film can be used to get the emission for all wells in series allowing a compact fluorometer. There can be one large absorbance filter also acting as an excitation filter. Since LEDs are low in cost, an array can be used. The use of opaque walls helps since if the plate is made of clear material the emission can also cause excitation of dyes in other wells. However, the light in the cover film (410) is going from each well to the end of cover film as shown in the exemplary embodiment of FIG. 4, thus guiding the light from each well towards the detector.

As an implementation of the optical technique, as shown in the exemplary embodiment of FIG. 4, a source which can excite multiple dyes can make multiplexing easy using simple optical equations, as known to the person skilled in the art. For instance, fluorescence resonance energy transfer (FRET) probes can be excited by a single wavelength, while having different emission peaks, due to different acceptor dyes. Measurements can be taken as follows:

a. Set the temperature to 95° C. (or wherever the baseline is required) and record fluorescence. This reading can be the baseline. It may also include a portion of excitation light. Moreover, the baseline can be time based as well (for instance, it can be the first cycle of qPCR/isothermal reaction).

b. For reference dyes the reading can be a portion of excitation light and some baseline.

c. Keep the excitation constant and measure the fluorescence at the reference temperature (e.g. an annealing temperature of 60° C.). Subtract the reference to calculate the emission. In many cases, the effect of extinction due to the dye's fluorescence can be ignored; otherwise that effect can be modeled and the reading can be corrected.

In several embodiments of the present disclosure, the sample area can be illuminated from the top, either normally to the sample surface, or at an angle to the normal. In several embodiments, the detectors can be placed on the side of the sample area. Such configurations can have several advantages, including but not limited to a compact design and an easier access to the sample area. The embodiments that use cartridges for the samples to be analyzed, the top illumination and side detection configuration can be advantageous as it can allow the cartridge to be easily inserted in the structure and the reflecting light to be efficiently collected at the sides. The cartridges can be designed to allow efficient collection from the sides of the structure. The side detection configuration can allow less light to reach the detector which does not carry information from the analyzed sample.

The examples set forth above are provided to those of ordinary skill in the art a complete disclosure and description of how to make and use the embodiments of the gamut mapping of the disclosure, and are not intended to limit the scope of what the inventor/inventors regard as their disclosure.

Modifications of the above-described modes for carrying out the methods and systems herein disclosed are obvious to persons of skill in the art and are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A system for optical detection comprising:
   a light source having a first side and a second side;
   a first optical filter having a first side and a second side, the first side of the first optical filter being substantially close to the second side of the light source;
   a collimation and/or guidance optics having a first side and a second side, the first side of the collimation and/or guidance optics being substantially close to the second side of the first optical filter;
   a second optical filter having a first side and a second side, the first side of the second optical filter being substantially close to the second side of the collimation and/or guidance optics;
   an optics to control stray light having a first side and a second side, the first side of the optics to control stray light being substantially close to the second side of the second optical filter;
   one or more absorbing layers attached to the second side of the optics to control stray light, wherein the one or more absorbing layers being partially covering the second side of the optics to control stray light, thus allowing the light from the light source to pass through;
   a chamber containing a sample to be illuminated, the chamber being contained in a cartridge comprising a reflector attached to a first side of the cartridge and a reflective layer attached to bottom of the cartridge, wherein the light emitted by the sample are reflected back to the sample by the reflective layer and guided by the reflector towards a second side of the cartridge; and
   a detector having a first side and a second side, the first side of the detector being substantially close to the second side of the cartridge, wherein the detector detects the light emitted by the sample.

2. The system of claim 1, wherein the detector further comprises a third optical filter and optics attached to the first side of the detector.

3. The system of claim 1, wherein the light source is chosen from a group comprising: a LED source, a high brightness LED source, a dye LED, an array of LED sources, a UV LED source, a laser diode, a laser light source, a vertical cavity surface emitting laser (VCSELs).

4. The system of claim 1, wherein the first optical filter is an absorbance or interference filter.

5. The system of claim 4, wherein the first optical filter is made from a group comprising of plastic, resin and glass.

6. The system of claim 1, wherein the cartridge is composed of a material with a higher index of refraction to trap more light inside the cartridge due to the critical angle.

7. The system of claim 6, wherein the cartridge is made of plastic or other polymer.

8. The system of claim 7, wherein the cartridge made of polymer guides light emitted from the sample to the second side of the cartridge by total internal reflection (TIR).

9. The system of claim 7, wherein the sides of the cartridge is convex shaped to guide light from side of the cartridge to the detector.

10. The system of claim 1, wherein the collimation and/or guidance optics is shaped to guide a homogenized and designed shaped beam to the chamber which can match the chamber shape.

11. The system of claim 1, wherein the collimation and/or guidance optics comprise waveguides.

12. The system of claim 1, further comprising an array of detectors.

13. The system of claim 1, wherein light rays emitted from the light source are incident on the sample at an angle.

14. The system of claim 1, wherein bottom of the chamber is composed of a clear polymer.

15. The system of claim 14, wherein the system further comprises a bottom absorbing layer placed substantially close to the bottom of the cartridge.

16. The system of claim 1, further comprising multiple chambers, each containing a sample to be illuminated.

17. The system of claim 16, wherein the multiple chambers are sandwiched between a cover film and the reflective layer attached to bottom of the cartridge.

18. The system of claim 17, wherein the cover film guides the light from the multiple chambers towards the detector.

19. The system of claim 1, wherein the first optical filter, the second optical filter, are removed.

20. The system of claim 1, wherein the system is used to perform qPCR and/or ELISA.

21. A method for optical detection, the method comprising:
   providing the system of claim 1;
   recording a first fluorescence signal at a first desired temperature;
   recording a second fluorescence signal with at a second desired temperature while keeping excitation constant; and
   subtracting the second fluorescence signal from the first fluorescence signal.

* * * * *